United States Patent [19]
Kammerer

[11] Patent Number: 5,807,320
[45] Date of Patent: Sep. 15, 1998

[54] BOTTLE SQUEEZING METHOD

[76] Inventor: K. Scott Kammerer, 4752 Springfield Dr., Dunwoody, Ga. 30338

[21] Appl. No.: 641,912

[22] Filed: May 2, 1996

[51] Int. Cl.⁶ .................................................. A61M 31/00
[52] U.S. Cl. ........................... 604/54; 604/134; 604/142; 222/96
[58] Field of Search .................................. 604/134, 142, 604/49, 54, 39, 131, 153, 214; 222/95, 96, 325–326

[56] References Cited

U.S. PATENT DOCUMENTS

| | | | |
|---|---|---|---|
| 2,595,493 | 9/1952 | Slaby et al. | 73/425.6 |
| 2,869,545 | 1/1959 | Forsyth | 128/232 |
| 4,273,505 | 6/1981 | Clark et al. | 414/735 |
| 4,790,587 | 12/1988 | Stoll | 294/119.3 |
| 4,909,790 | 3/1990 | Tsujikawa et al. | 604/132 |
| 5,018,776 | 5/1991 | Trygg | 294/119.3 |
| 5,032,115 | 7/1991 | Hakansson et al. | 604/142 |
| 5,061,239 | 10/1991 | Shiels | 604/26 |
| 5,063,797 | 11/1991 | Huang | 81/60 |
| 5,090,758 | 2/1992 | Lord | 294/98.1 |
| 5,090,759 | 2/1992 | Sato et al. | 294/119.3 |
| 5,322,070 | 6/1994 | Goodman et al. | 128/747 |
| 5,328,477 | 7/1994 | Sitko | 604/134 |
| 5,337,925 | 8/1994 | Ferrara, Jr. | 222/214 |
| 5,364,146 | 11/1994 | Brandorff et al. | 294/86.4 |
| 5,372,786 | 12/1994 | Iles | 422/104 |
| 5,405,319 | 4/1995 | Abell et al. | 604/27 |
| 5,409,167 | 4/1995 | Borod | 239/152 |
| 5,419,772 | 5/1995 | Teitz et al. | 604/142 |

FOREIGN PATENT DOCUMENTS 2229636  10/1990  United Kingdom ................. 604/134

OTHER PUBLICATIONS

Freeman Equipment Company; Series 2600 Miniflex Valves 1992.

Ableware®; pp. 19 & 53 [3 Products Shown—MADDA-GRIP® Built–Up Grip; Anus Stimulator; Suppository Inserter].

*Primary Examiner*—Mark Bockelman
*Attorney, Agent, or Firm*—Isaf, Vaughan & Kerr

[57] ABSTRACT

A receptacle receives and at least partially contains a container that contains fluid. The receptacle, or the receptacle in combination with the container, defines an inflation device. The inflation device is associated with the container so that when the inflation device is inflated the fluid is forced from the container. Subsequent to the proper positioning of the container relative to a human cavity, the inflation device is inflated by operating an activation device such as a switch or a valve. The activation device is preferably distant from the container and receptacle such that the activation device can be easily accessed and operated. Alternatively a spring is associated with the receptacle. The spring is compressed and a retention device operates to maintain the spring in the compressed configuration. Once the container and receptacle are properly positioned relative to a cavity, the retention device is acted upon to release the spring. The receptacle and bottle are constructed and arranged so that the resulting expansion or movement of the spring affects compression of the container such that the fluid is ejected from the container. A switch or lever is preferably linked to and operates the retention device. The switch is preferably distant from the container and receptacle such that the switch can be easily accessed and operated.

3 Claims, 12 Drawing Sheets

BOTTLE SQUEEZING METHOD

BACKGROUND OF THE INVENTION

The present invention relates generally to the field of applicators, and more particularly to the field of applicators for injecting fluids into a body cavity.

Applicators for injecting fluids into a body cavity are well known and are typically used, for example and not limitation, for enemas and douches. Such applicators can be characterized as including a container defining a container chamber for containing the fluid and an elongated nozzle connected to and extending from the container for insertion into the cavity. The container is typically constructed of a flexible material so that it can be manually collapsed to force the fluid out of the container through the nozzle and into the cavity.

An applicator for providing enemas is disclosed in U.S. Pat. No. 2,869,545. In that device, a valve-like member is interposed between the container and the nozzle to control fluid flow. The valve is acceptably in the form of a disc which defines a diametrical slit which extends substantially across the disk. The valve seeks to preclude leakage from the container when the container is inverted but not compressed, and further seeks to preclude back-flow into the container.

The above-described applicators provide a very convenient and effective means for the average person to provide themselves with an enema or douche. However, there is a class of persons, such as partially disabled persons, that have the some dexterity yet lack the strength necessary to manually compress the container in a manner that provides the desired result. As a result, these persons must seek the assistance of another when an enema or douche is desired or necessary. This is unfortunate for those who would prefer to privately provide themselves with an enema or douche.

There is, therefore, a need in the industry for an apparatus and method that seeks to allow those with minimal strength and/or dexterity to provide themselves with a convenient enema or douche, or the like.

SUMMARY OF THE INVENTION

Briefly described, the present invention comprises a method and apparatus for forcing a fluid or the like, out of a container. In accordance with the preferred embodiment of the present invention, a method and apparatus are provided for automating the process of providing an enema or douche, or the like. A method and apparatus are provided that automatically compresses a container with fluid therein so that the fluid exits the container with sufficient force to provide a satisfactory enema, douche, or the like.

In accordance with the preferred embodiments of the present invention, a receptacle receives and at least partially contains a container that contains the necessary fluid, and a strap or other device is preferably associated with the receptacle to facilitate the proper positioning of the container with respect to a target human cavity. In accordance with certain embodiments of the present invention, the receptacle, or the receptacle in combination with the container, defines an inflation device. The inflation device is preferably in the form of a distensible chamber or a chamber associated with and partially defined by a piston. The inflation device is associated with the container so that when the inflation device is inflated, the fluid is forced from the container.

In accordance with certain embodiments, inflation is achieved by operating a valve that is preferably interposed and provides communication between the inflation device and a source of pressurized medium.

The valve is preferably distant from the container and receptacle such that the valve can be easily accessed and operated. In accordance with another embodiment, inflation is achieved by turning on a compressor that is in communication with the inflation device. An "on/off" switch, or the like, for the compressor is preferably distant from the container and receptacle such that the "on/off" switch can be easily accessed and operated. Subsequent to the inflation of the inflation device and the forcing of the fluid from the container, the container is moved away from the cavity and the inflation device is deflated.

In accordance wither certain other embodiments of the present invention, a spring is associated with the receptacle. The spring is compressed and a retention device operates to maintain the spring in the compressed configuration. Once the container and receptacle are properly positioned relative to a cavity, the retention device is acted upon to release (i.e., activate) the spring. The receptacle and bottle are constructed and arranged so that the resulting expansion or movement of the spring affects compression of the container such that the fluid is ejected from the container. The retention device is preferably connected to the receptacle. A switch or lever is preferably linked to and operates the retention device. The switch is preferably distant from the container and receptacle such that the switch can be easily accessed and operated.

It is, therefore, an object of the present invention to automatically eject fluid or the like from a container.

Another object of the present invention is to at least partially automate the process of providing an enema or douche.

Yet another object of the present invention is to enable persons with minimal dexterity and/or strength to provide themselves with douches or enemas.

Still another object of the present invention is to enable partially disabled persons to be less reliant upon the assistance of others.

Other objects, features, and advantages of the present invention will become apparent upon reading and understanding this specification, when taken in conjunction with the accompanying drawings.

DETAILED DESCRIPTION OF THE PREFERRED EMBODIMENTS

Figure 1:
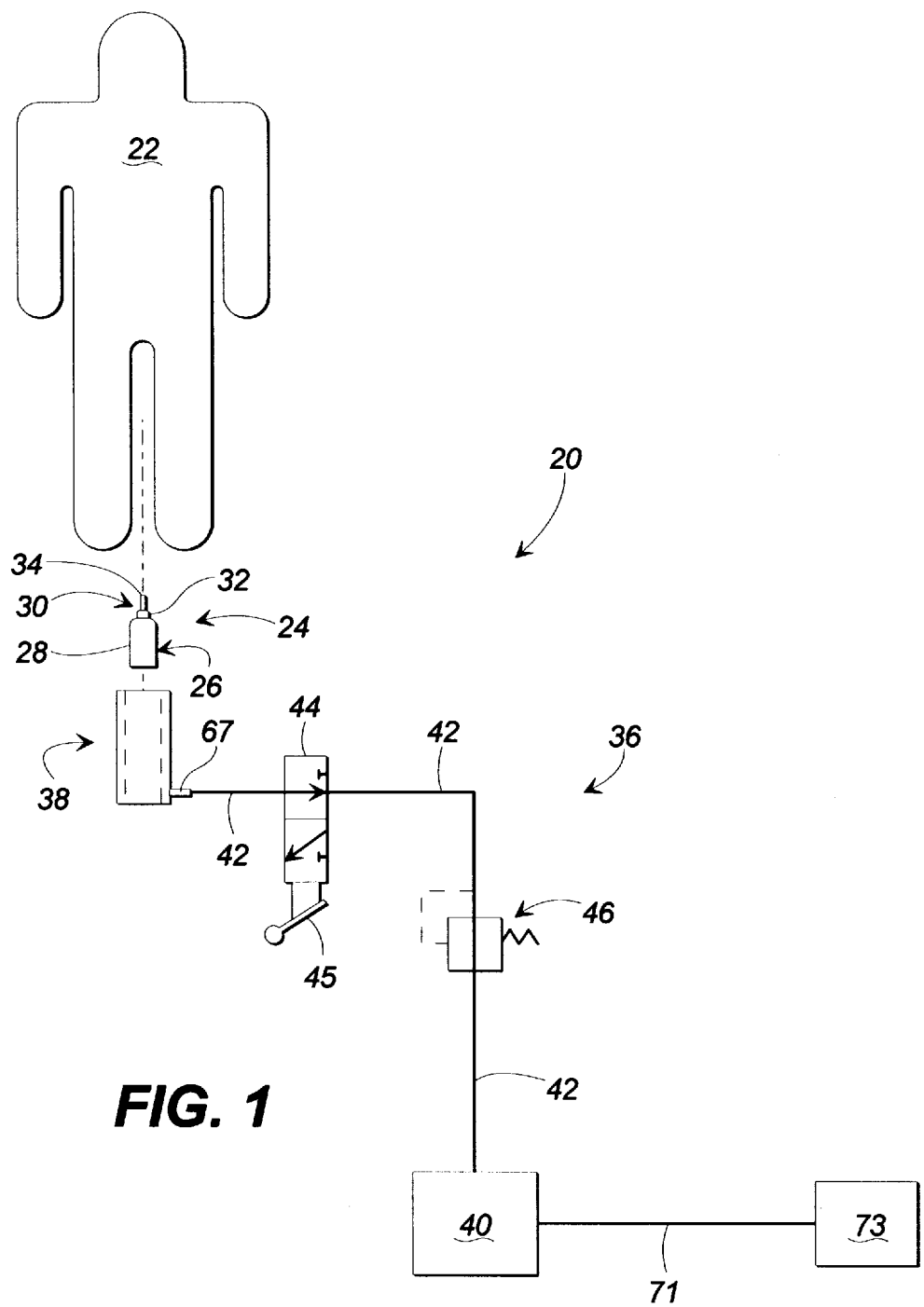
FIG. 1 is a schematic diagram of an applicator assembly proximate to a person, in accordance with a first preferred embodiment of the present invention.

Referring now in greater detail to the drawings in which like numerals represent like components throughout the several views, FIG. 1 is a schematic diagram of an applicator assembly 20 proximate to a person 22, in accordance with a first preferred embodiment of the present invention. The applicator assembly includes a container assembly 24, an acceptable example of which is disclosed in U.S. Pat. No. 2,869,545, which patent is expressly incorporated herein by reference, in its entirety. However, the present invention is not limited to the container assembly disclosed in the aforementioned patent, as various containers and container assemblies are within the scope of the present invention. The container assembly 24 includes a container 26 having a wall 28 that at least partially bounds and defines a chamber within the container 26 for containing a fluid. The wall further defines a neck and an opening to the chamber within the container 26 which are not seen in FIG. 1. The container assembly 24 further includes a nozzle 30 having a cap 32 formed at one end thereof. The cap 32 fits over the aforementioned neck and opening to the chamber within the container 26 such that the neck and opening are not seen in FIG. 1. The nozzle 30 defines a nozzle passage therethrough that is in fluid communication with the aforementioned opening a nozzle opening 34 that is defined by the nozzle 30 opposite from the cap 32.

In accordance with the first preferred embodiment of the present invention, the applicator assembly 20 further includes a compressing device 36 having a receptacle 38 that receives and compresses the container 26 to force the fluid out of the container through the nozzle opening 34, as discussed in greater detail below. The compressing device 36 further includes a source 40 of pressurize medium and a device, such as a conduit 42 or tubing, for connection to a fitting 67 associated with the receptacle 38 to place the source 40 in fluid communication with the receptacle 38, as discussed in greater detail below. The source 40 is preferably a source of inert gas at a pressure of at least 40 pounds per square inch (psig.). More particularly, for example and not limitation, the source 40 is acceptably a storage tank that is filled with pressurized gas. The applicator assembly 20 also preferably further includes a valve 44, or the like, communicating with the compressing device 36 for controlling or activating the compression device 36 by selectively placing the receptacle 38 in fluid communication with the source 40, and venting the receptacle 38 to the atmosphere, as discussed in greater detail below. The valve 44 is preferably a type of valve that can be easily operated and preferably includes an operator for controlling the functioning of the valve 44. The operator for controlling the valve 44 is depicted as a manual handle 45 in FIG. 1. For example and not limitation, the valve 44 is acceptably a spool-like slide valve, or an electric solenoid operated valve. It is also preferable to associate a pressure regulator 46 with the compressing device 36. The pressure regulator 46 functions in a manner that seeks to ensure that the medium supplied to the receptacle 38 for inflation purposes is at approximately 40 psig. A pressure regulator 46 need not be employed when a source 40 is employed that is capable of constantly providing the desired pressure. However, the present invention is not intended to be limited to any particular pressure range, and the exact operating pressures will be dictated by various factors that should be understood by those skilled in the art. As depicted in FIG. 1, the valve 44 and regulator 46 are interposed within the conduit 42.

Figure 2:
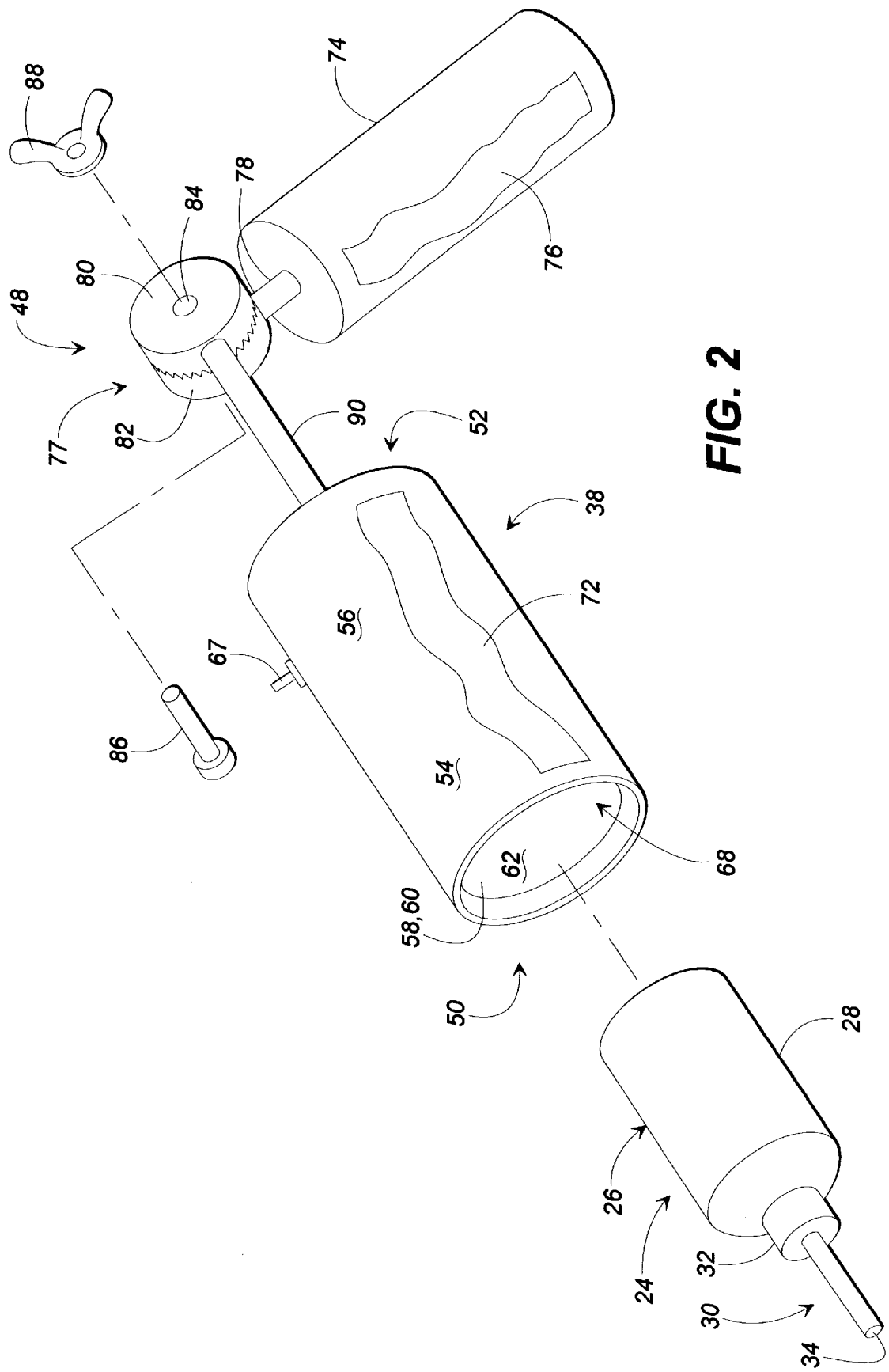
FIG. 2 is an exploded perspective view of a container assembly exploded away from a receptacle and supplemental handle assembly, in accordance with the first preferred embodiment of the present invention.

FIG. 2 is an exploded perspective view of the container assembly 24 exploded away from the receptacle 38, in accordance with the first preferred embodiment of the present invention. As depicted in FIG. 2, the receptacle 38 is accessorized with a supplemental handle assembly 48. The supplemental handle assembly 48 is not necessarily associated with the receptacle 38 of the first preferred embodiment, but in accordance with alternate embodiments of the present invention the supplemental handle assembly 48 is associated with the receptacle 38 as depicted in FIG. 1. In other alternate embodiments of the present invention the handle assembly 48 is similarly connected to each of the devices disclosed below that correspond to the receptacle 38.

Figure 3:
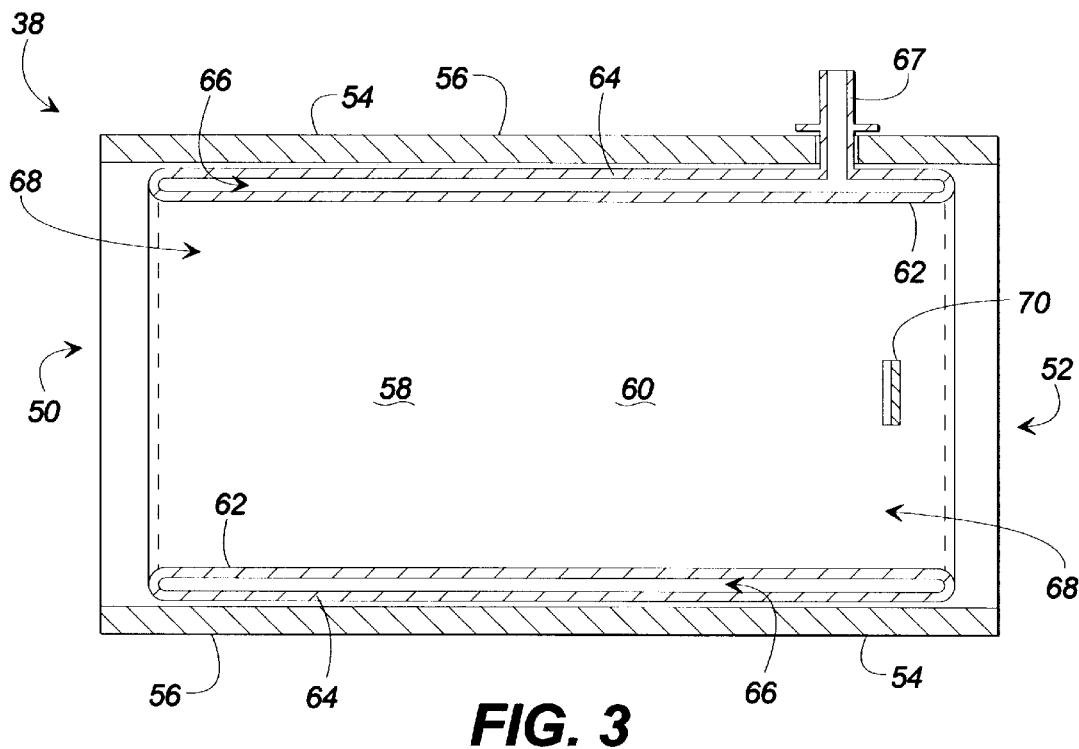
FIG. 3 is an isolated, side cross-sectional, schematic view of portions of the receptacle of FIG. 2.
Figure 4:
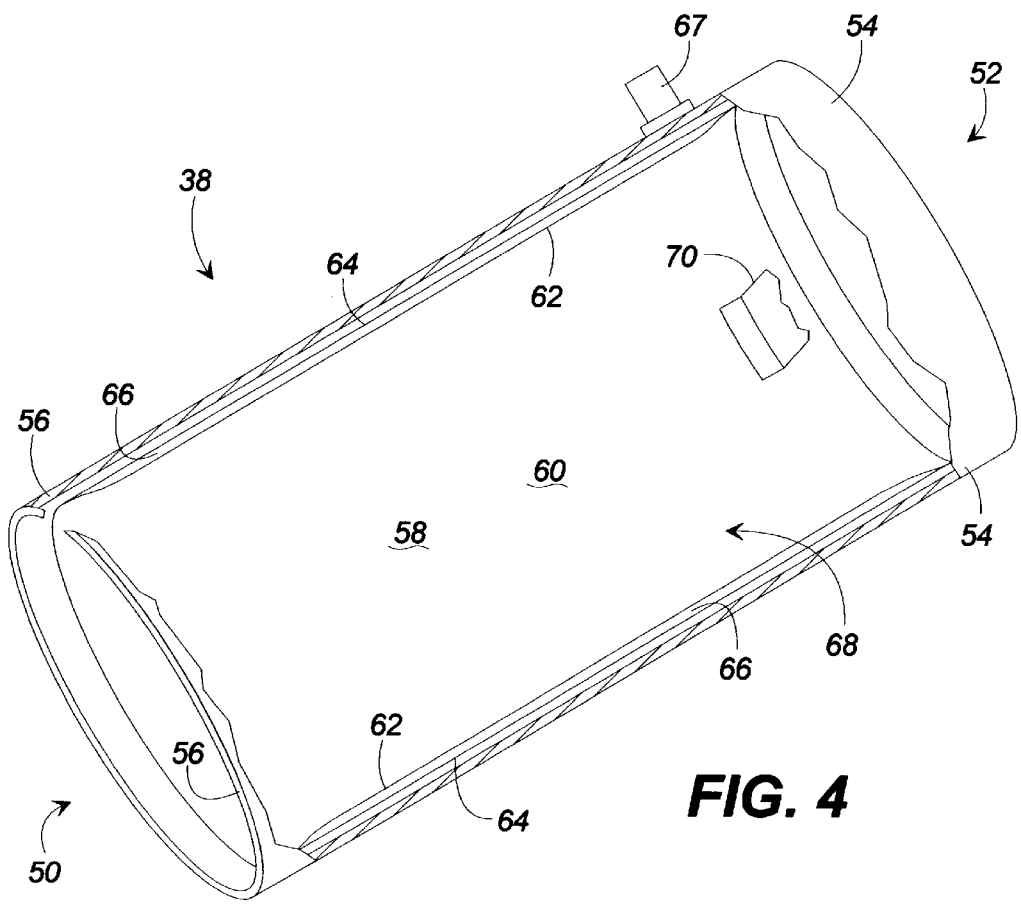
FIG. 4 is an isolated, perspective, partially cutaway, schematic view of the receptacle of FIG. 2.

FIG. 3 is an isolated side cross-sectional, schematic view of portions of the receptacle 38 in accordance with the first preferred embodiment of the present invention. FIG. 4 is an isolated, perspective, partially cut-away, schematic view of the receptacle 38, in accordance with the first preferred embodiment of the present invention. Referring primarily to FIGS. 3 and 4, the receptacle 38 includes a front end 50 and a rear end 52, and further includes an annular, generally rigid, and generally non-distensible outer wall 54 that is depicted in the form of an outer tube 56 that is open at the ends 50,52. The outer wall 54 is acceptably constructed from a relatively rigid plastic material, or aluminum, or the like. A double walled bladder or distensible inflation device 58 that is depicted in the form of an internal tube 60 is internal to and extends coaxially with the outer tube 56, and is open at the ends 50,52. The inflation device 56 includes a distensible annular inner wall 62 and a distensible annular intermediate wall 64 that are joined or contiguous at the ends 50,52 such that a generally annular inflation chamber 66 is defined within the inflation device 56. the inflation device 56 is acceptably constructed from rubber such as, but not limited to, the inflatable rubber from which inner tubes for tires are made, or the like. A nozzle-like fitting 67 extends through an aperture in the outer wall 54 and is connected to the inflation device 58 and in fluid communication with the inflation chamber 66.

The inner wall 62 at least partially bounds and defines a receptacle cavity 68 that is open at the ends 50,52. In accordance with all of the preferred embodiments of the present invention, the receptacle cavity 68 is at least partially occluded at the rear end 52. Such occlusion is acceptably achieved, for example and not limitation, with a cap or plug, or the like. As partially depicted in FIG. 4, partial occlusion of the receptacle cavity 68 is achieved by way of an internal strap 70 that spans across the receptacle cavity 68 proximate to the rear end 52. As partially depicted in FIG. 4, the strap 70 preferably includes opposite ends that are connected, respectively, to diametrically opposed portions of the inner wall 62. The strap 70 is not seen in FIG. 2. The strap 70 is partially cross-sectioned in FIG. 3, and the strap 70 is partially cut-away in FIG. 4. Referring to FIGS. 3 and 4, the entire exterior surface of the intermediate wall 64 preferably abuts and is preferably bonded, for example by glue, to the interior surface of the outer wall 54, but such abutting and bonding is not shown in an effort to clarify the views.

Referring to FIG. 2, another strap 72 is preferably attached to the exterior of the outer wall 54. Opposite ends of the strap 72 are preferably attached to the outer wall so that the fingers or palm of a user of the receptacle 38 can be interposed between the mid-span of the strap 72 and the outer wall 54 such that the strap 72 seeks to make it easier for a user to grip or hold onto the receptacle 38, as discussed in greater detail below. Each of the devices discussed below that correspond to the receptacle 38 are preferably similarly equipped with a strap 72.

Referring back to FIG. 1, the applicator assembly 20 is easily operated by those with limited dexterity or strength. Initially, the valve 44 is operated to define a non-inflated configuration so that the valve 44 fluidly isolates the source 40 from the receptacle 38, and the valve 44 further vents the inflation chamber 66 (FIGS. 3 and 4) to the atmosphere. Then, a filled container assembly 24 is inserted into the receptacle cavity 68 as far as possible such that the end of the container 26 abuts the strap 70 (FIGS. 3 and 4) and the nozzle 30 extends from the receptacle cavity 68. Then the receptacle 38 is manipulated, for example by utilizing the strap 72 (FIG. 2), to insert the nozzle 30 into the desired human cavity. Once the nozzle 30 is properly inserted into the proper human cavity, the valve 44 is operated so that the valve 44 places the source 40 in communication with the inflation chamber 66, whereby the inflation device 58 is inflated and expands to compress the container 26 such that the fluid is forced out of the container 26 through the nozzle 30, whereby the desired result is achieved. Then the receptacle 38 and the container 26 therewith are moved away from the human cavity and the valve 44 is returned to the non-inflated configuration to allow the container assembly 24 to be withdraw from the receptacle 38. Then, if desired, another filled container assembly 24 is properly positioned within the receptacle 38 such that the applicator assembly 20 is ready for reuse.

The valve 44 is preferably mounted or positioned where it can be readily accessed during this process. For example, the valve 44 can be mounted to the headboard of a bed such that a user can easily operate the valve 44 by taping the handle 45 with his or her head while the receptacle 38 and associated container 26 are being handled proximate to the middle portion of the bed and the user's posterior.

Referring further to FIG. 1, the arrangement and operations outlined above are preferred when the source 40 is a storage tank that is filled with pressurized gas. However, the source 40 is also acceptably, for example and not limitation, a compression machine (i.e., a compressor, or more particularly a machine that increases the pressure of a gas). When the source 40 is in the form of a compression machine the source 40 preferably has an "off/on" switch 73 connected thereto for activating and deactivating the source 40 (i.e., compression machine). The switch 73 is preferably remote from the source 40 and communicates electrically with the source 40 by way of wiring 71 so that the switch 73 can be mounted for use in a manner similar to that discussed above for the valve 44.

When the source 40 is in the form of a compression machine that is controlled by a switch 73, it is in some cases preferable not to include the valve 44 in the applicator assembly 20. Accordingly, the inflated configuration is achieved by turning the source 40 (i.e., compression machine) "on" by properly operating the switch 73, and the non-inflated configuration is achieved by turning the source 40 (i.e., compression machine) "off" by properly operating the switch 73. The immediately foregoing assumes that the source 40 (i.e., compression machine) is constructed and arranged so that when it is "off", it vents to the atmosphere, whereby the inflation device 58 (FIGS. 2–4) would vent to the atmosphere though the source 40 (i.e., compression machine). If the source 40 (i.e., compression machine) is constructed and arranges so that it does not vent to the atmosphere when it is "off", it would be desirable to have the valve 44, or another type of valve, communicating with the conduit 42 to facilitate venting of the inflation device 58 to the atmosphere.

Referring back to FIG. 2, the supplemental handle assembly 48 seeks to aid in the positioning of the receptacle 38. the assembly 48 acceptably includes a generally cylindrical handle member 74 having a strap 76. The opposite ends of the strap 76 are connected to the handle member 74, or member 78, so that the fingers or palm of a user of the receptacle 38 can be interposed between the mid-span of the strap 76 and the outer surface of the handle member 74 such that the strap 76 seeks to make it easier for a user to grip or hold onto the handle member 74 to control the placement of the receptacle 38 and thereby the nozzle 30.

A selective pivoting assembly 77 connects the handle member 74 to the receptacle 38. A rod 78 is connected between the handle member 74 and a plate 82 that has a textured face. A plate 80 also has a textured face for mating with the textured face of the plate 82, as depicted in FIG. 2. A mounting bracket or rod 90 is connected between the plate 80 and the outer wall 54 of the receptacle 38. A bore 84 extends through both of the plates 80,82, and a threaded bolt 86 extends through the bore 84 and receives a nut 88 to force the plates 80,82 together and preclude pivoting of the plates 80,82 relative to another. The nut 88 is loosened and the plates 80,82 are pivoted to achieve a desired relationship between the handle member 74 and the receptacle 38, and then the nut 88 is tightened to maintain the desired relationship.

Figure 5:
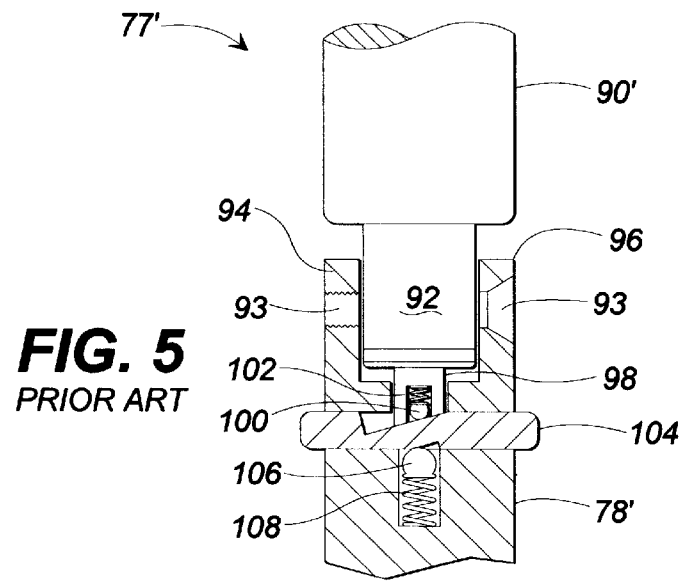
FIG. 5 is a cut-away, partially cross-sectioned view of a portion of a pivot assembly that takes the place of the pivot assembly of the supplemental handle assembly depicted in FIG. 2, in accordance with an alternate embodiment of the present invention.

FIG. 5 is a cut-away, partially cross-sectioned view of a portion of a pivot assembly 77' that takes the place of the plates 80,82, bolt 86, and nut 88 of the pivot assembly 77 of FIG. 2, in accordance with another alternate embodiment of the present invention. The rod 90' terminates in the form of a notched head 92 that is pivotally connected by a bolt 93 or the like between prongs 94,96 at the end of the rod 78'. A hollow peg 98 is forced by a ball 100 and spring 102, which are disposed within the peg 98, to engage notches defined in the head 92 to preclude pivoting between the rods 78',90'. As depicted in FIG. 5, by pushing a peg 104 to the right the peg 98 "falls" into a notch defined in the top of the peg 104 such that the peg 98 is disengaged from the notches in the head 92 and the rods 78',90' can be pivoted. Once the rods 78',90' are pivoted to the desired position, and as depicted in FIG. 5, the peg 104 is pushed to the left so that the peg 90 engages the notches in the head 92. A ball 106 is forced by a spring 108 into a notch defined in the bottom of the peg 104 to maintain the position of the peg 104, whereby the rods 78',90' are maintained in the desired position.

Figure 6:
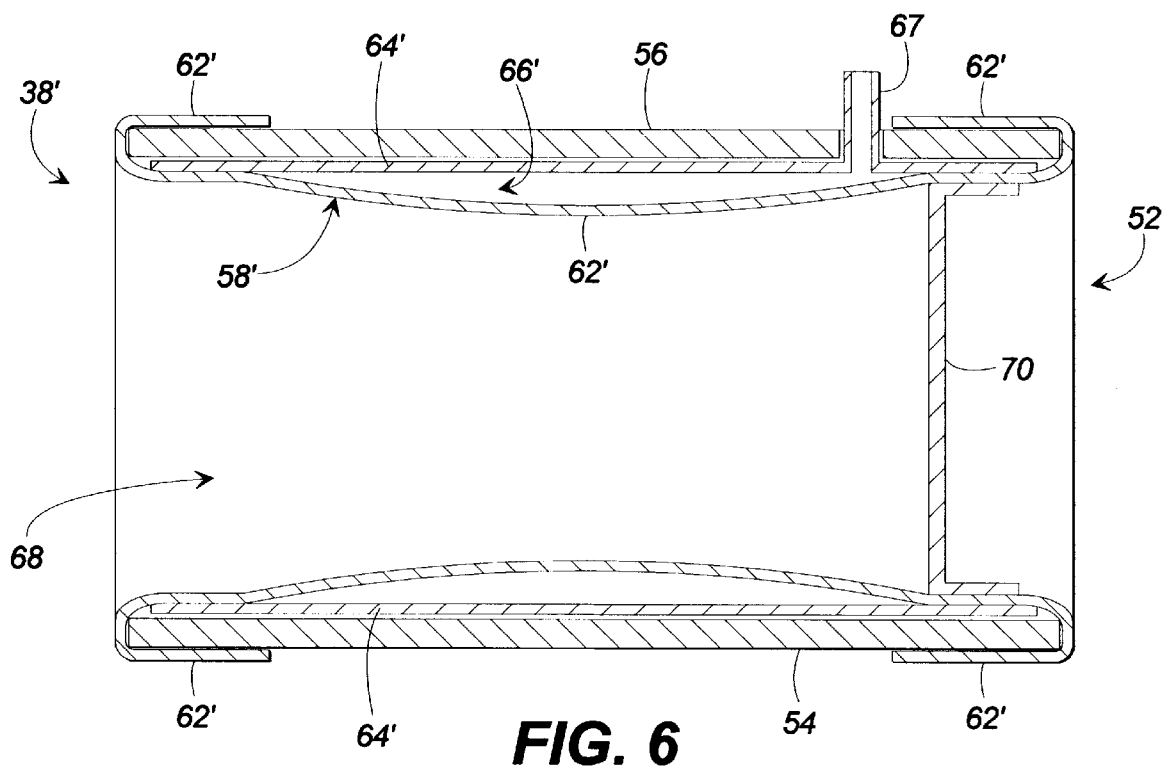
FIG. 6 is an isolated, side cross-sectional, schematic view of portions of a receptacle in accordance with a second preferred embodiment of the present invention.

FIG. 6 is an isolated side cross-sectional, schematic view of portions of a receptacle 38' that is used in place of the receptacle 38 of FIG. 1 in accordance with a second preferred embodiment of the present invention. The receptacle 38' of the second preferred embodiment is identical to the receptacle 38 (FIGS. 1–5) of the first preferred embodiment except for the noted variations in the inflation device 58' and the manner in which the inflation device 58' is connected to the outer tube 56. The inflation device 58' is inserted into the tube 56 and then the ends of the inner wall 62' are connected to the exterior surface of the outer wall 54 as shown. A strap 70 is fully seen connected between diametrically opposed internal surfaces of the inner wall 62.

Figure 7:
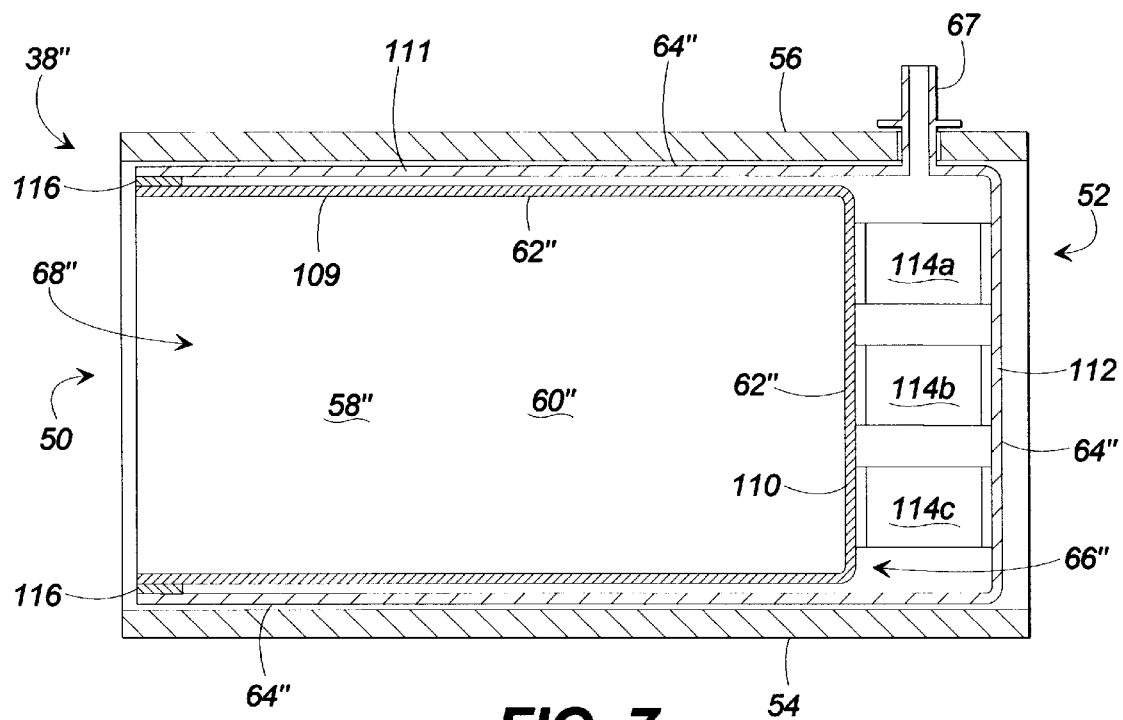
FIG. 7 is an isolated, side cross-sectional, schematic view of portions of a receptacle in accordance with a third preferred embodiment of the present invention.

FIG. 7 is an isolated side cross-sectional, schematic view of portions of a receptacle 38" that is used in place of the receptacle 38 of FIG. 1 in accordance with a third preferred embodiment of the present invention. The receptacle 38" of the third preferred embodiment is identical to the receptacle 38 (FIGS. 1–5) of the first preferred embodiment except for the noted variations in the inflation device 58". The inflation device 58" does not need to include a strap 70 (FIGS. 4 and 6) because the inflation device 58" itself occludes the rear end 52 of the receptacle cavity 68. That is, the walls 62",64" of the inflation device 58" each define a hollow cylinder 109,111, respectively, and generally circular disks 110,112, respectively, that close off the cylinders 109,111, respectively, at the rear end 52 of the receptacle 38". The disks 110,112 are connected by straps 114a–c or the like that are internal to the inflation chamber 66" and keep the inflation device 58" from pushing the container assembly 24 (FIGS. 1 and 2) out of the receptacle cavity 68" when the inflation device 58" is inflated. An annular ring 116 is preferably connected between the walls 62",64" at the front end 50 of the receptacle 38" to enclose the inflation chamber 66".

Figure 8:
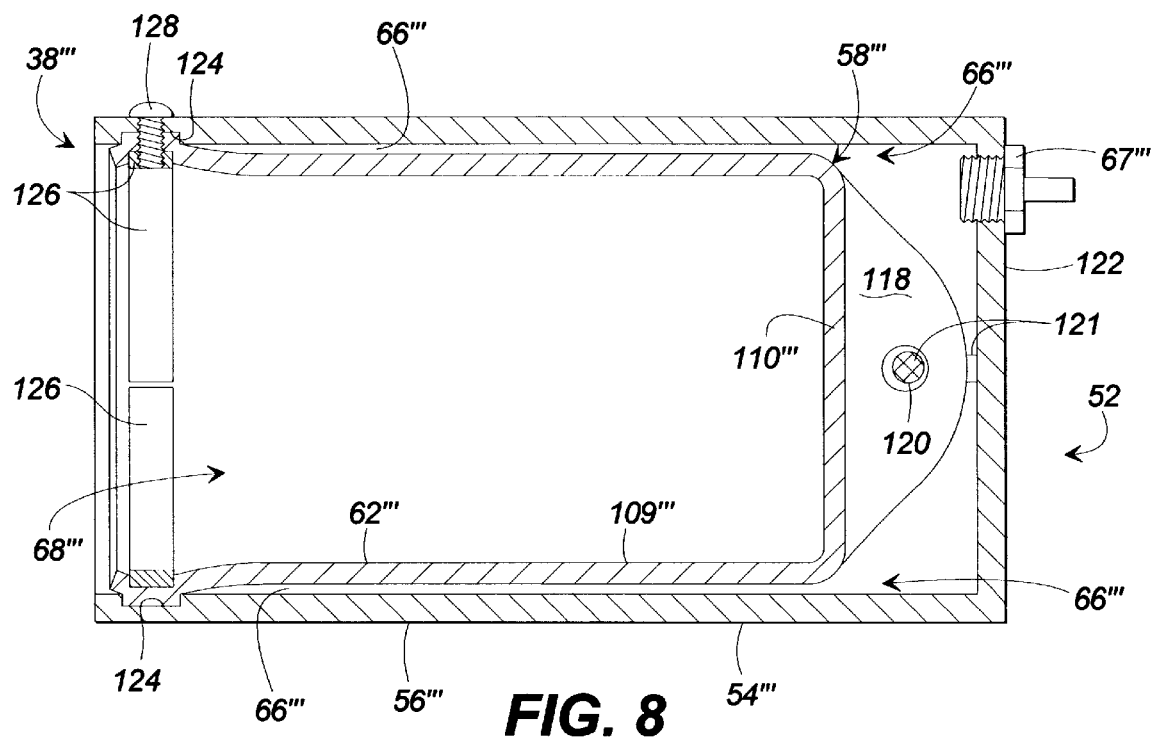
FIG. 8 is an isolated side cross-sectional, schematic view of portions of a receptacle in accordance with a fourth preferred embodiment of the present invention.

FIG. 8 is an isolated side cross-sectional, schematic view of portions of a receptacle 38''' used in place of the receptacle 30 of FIG. 1 in accordance with a fourth preferred embodiment of the present invention. The receptacle 38''' of the fourth preferred embodiment is identical to the receptacle 38 (FIGS. 1–5) of the first preferred embodiment except for the noted variations. The inflation device 58''' does not need to include a strap 70 (FIGS. 4 and 6) because the inflation device 58''' itself occludes the rear end 52 of the receptacle cavity 68'''. The inflation device 58''' includes solely the inner wall 62''' which defines a hollow cylinder 109''' and a generally circular disk 110''' that closes off the cylinders 109''' at the rear end 52 of the receptacle 38'''. The disk 110 includes or is contiguous with a tab 118 that extends toward the rear end 52 and defines a connection hole 120. A hook 121 extends into the hole 120 and thereby secures the tab 118 and the inflation device 58''' within the outer tube 56'''. The outer tube 56''' includes a rear wall 122 that spans between the rear periphery of the outer wall 54''', and the hook 121 is connected to and extends from the rear wall 122.

The outer tube 56''' defines an internal annular channel 124 into which the inner wall 62''' is forced by, for example, a split and expanding annular ring 126 that expands to secure the ring 126 and inner wall 62''' into the channel 124. As depicted in FIG. 8, a screw 128 further cooperates with the ring 126 to secure the ring 126 within the channel 124. By virtue of the construction and arrangement of the receptacle 38''', the inflation chamber 66''' is defined between the outer wall 54''', rear wall 122, and inner wall 62'''. A fitting 67''' is connected through the rear wall 122 and provides substantially the sole communication path with the inflation chamber 66'''.

Figure 9:
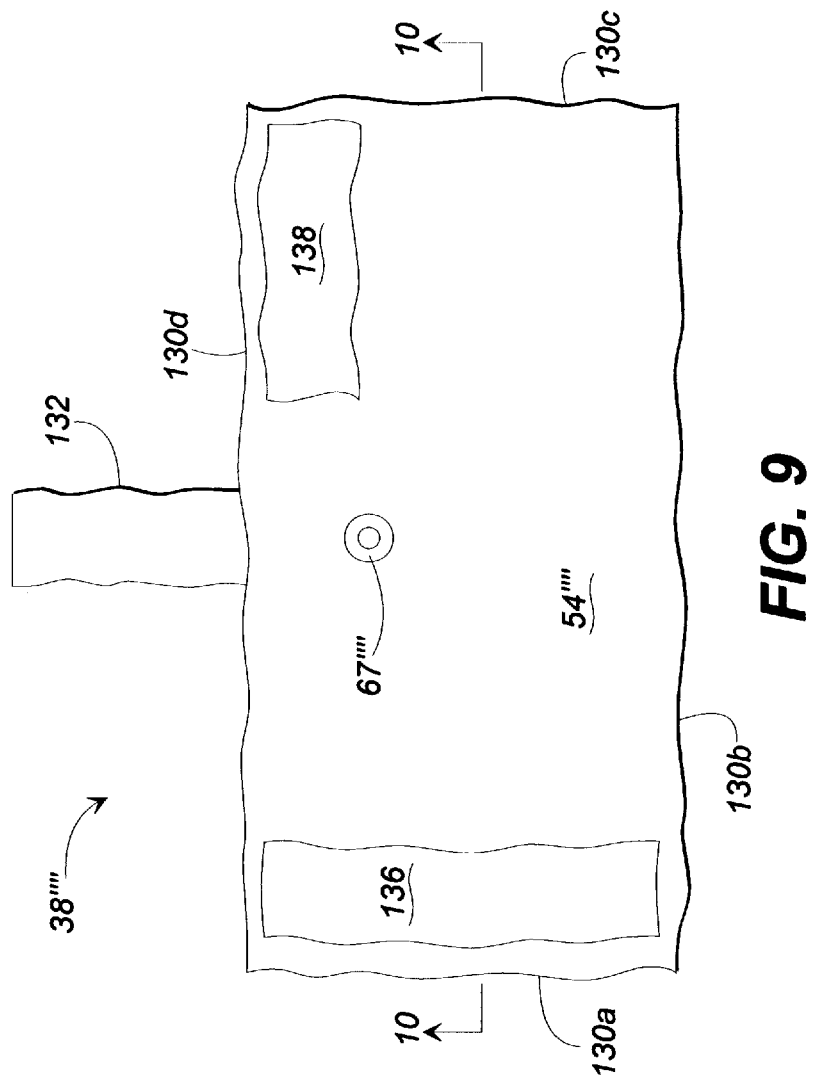
FIG. 9 is an isolated, schematic, top plan view of a receptacle in an open configuration, in accordance with a fifth preferred embodiment of the present invention.
Figure 10:
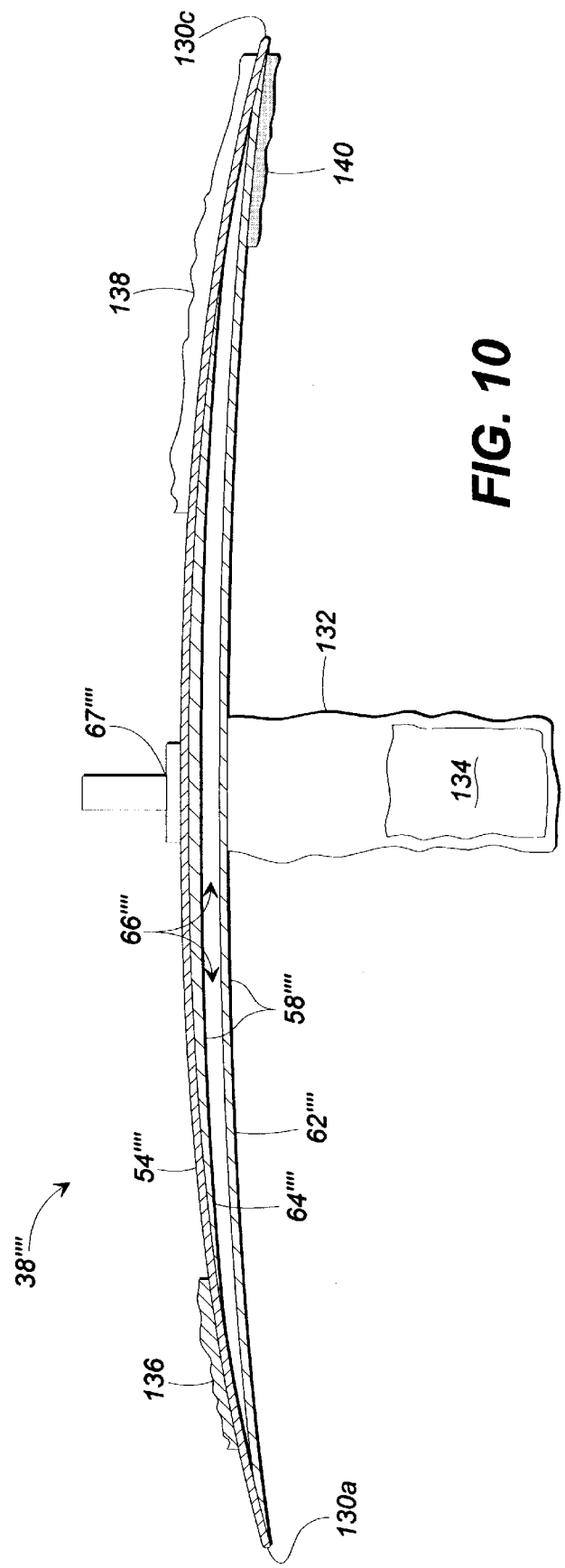
FIG. 10 is an isolated, schematic, cross-sectional view of the receptacle of FIG. 9, taken along line 10—10 of FIG. 9.

FIG. 9 is an isolated, schematic, top plan view of a receptacle 38'''' in an open configuration and FIG. 10 is an isolated, schematic, cross-sectional view of the receptacle 38'''', in accordance with a fifth preferred embodiment of the present invention. Once the receptacle 38'''' is configured to define a receptacle cavity (for example see the receptacle cavity 68 of FIG. 3), the receptacle 38'''' is used in place of the receptacle 38 of FIG. 1. The receptacle 38'''' includes edges 130a–d, and an inflation device 58'''' (FIG. 10) that includes a generally rectangular and distensible inner wall 62'''' (FIG. 10) and a generally rectangular intermediate wall 64'''' (FIG. 10) that are joined at the edges 130a–d to define the inflation chamber 66'''' between the walls 62'''',64''''. Referring to FIG. 10, a generally rectangular, somewhat flexible, yet generally non-distensible outer wall 54'''' is bonded to the exterior surface of the intermediate wall 64. The outer wall 54'''' is acceptably constructed of a material such as, but not limited to, a fabric such as nylon or polyester. A fitting 67'''' extends through the outer wall 54'''' and preferably provides the sole communication path with the inflation chamber 66''''.

A strap 132 is connected to and extends from the edge 130d. The strap 132 includes a connecting device, which is acceptably in the form of a patch 134 of hook and loop material such as that sold under the trade name VELCRO, attached thereto. Similar patches 136, 138 are connected to the exterior surface of the outer wall 54, and a similar patch 140 is connected to the exterior surface of the inner wall 62. The receptacle 38'''' is bent and the patch 140 is connected to the patch 136 so that the inner wall 62'''' generally encircles and defines a receptacle cavity (for example see receptacle cavity 68 of FIG. 3). Then, the patch 134 is connected to the patch 138 to at least partially occlude one of the openings to the formed receptacle cavity.

Figure 11:
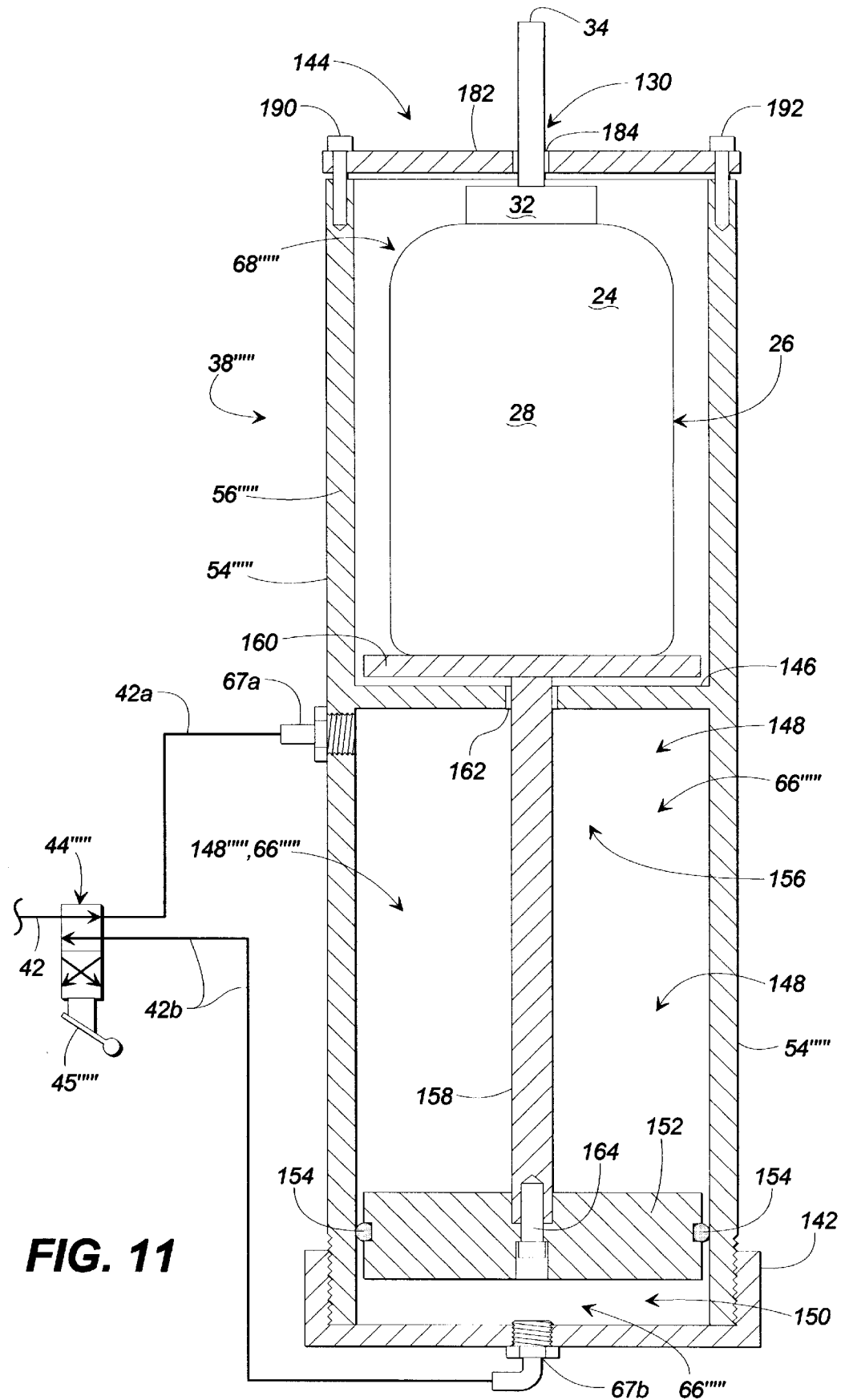
FIG. 11 is a schematic diagram of a valve, a portion of conduit, and a cross-sectioned receptacle with a container assembly therein, in accordance with a sixth preferred embodiment of the present invention.

FIG. 11 is a schematic diagram of a valve 44''''', a portion of the conduit 42 (also see FIG. 1), conduits 42a,b, and a cross-sectioned receptacle 38''''' with a container assembly 24 therein, in accordance with a sixth preferred embodiment of the present invention. In accordance with the sixth preferred embodiment of the present invention, the components depicted in FIG. 11 replace the corresponding components depicted in FIG. 1. The receptacle 38''''' includes an outer wall 54''''' that is in the form of an outer tube 56''''' that generally defines an internal bore. A cap 142 acceptably threads onto and occludes one end of the tube 56''''' and a removable plate assembly 144 removably occludes the other end of the tube 56'''''. The removable plate assembly 144 includes a plate 182 and bolts 190,192, and is discussed in greater detail below. A partition 146 extends inward from the internal surface of the tube 56''''' to generally bisect the bore of the tube 56''''' and at least partially define a receptacle cavity 68''''' internal to the tube 56''''' toward one end of the tube 56''''' and an inflation chamber 66''''' internal to the tube 56''''' toward the opposite end of the tube 56'''''.

The inflation chamber 66''''' is divided into a first chamber 148 and a second chamber 150 by a piston 152 and an accompanying annular piston ring 154 that isolate the chambers 148,150 from one another. The piston 152 and ring 154 are together capable of moving toward and away from the opposite ends of the receptacle 38'''' to inversely vary the sizes of the chambers 148,150. The receptacle 38'''' is constructed and arranged such that the chambers 148,150 are generally airtight, except for the fact that a fitting 67a provides substantially the sole communication path with the chamber 148 and a fitting 67b provides substantially the sole communication path with the chamber 150.

A linkage or plunger assembly 156 transfers movement of the piston 152 to compress and eject fluid from the container 26. The plunger assembly 156 includes a rod 158 that is acceptably connected to the piston 152 by a bolt 164 or the like. The rod 158 extends from the piston 152 in a sealed fashion through an aperture 162 defined through the partition 146. A plate 160 is connected to the rod 158 opposite from the piston 152. The plate 160 is for contacting and compressing the container 26 in response to movement of the piston 152. In operation, the valve 44'''' functions to place the chamber 148 in communication with the source 40 (FIG. 1) and vent the chamber 150 to the atmosphere, and visa versa, which causes the piston 152 to stroke.

Figure 12:
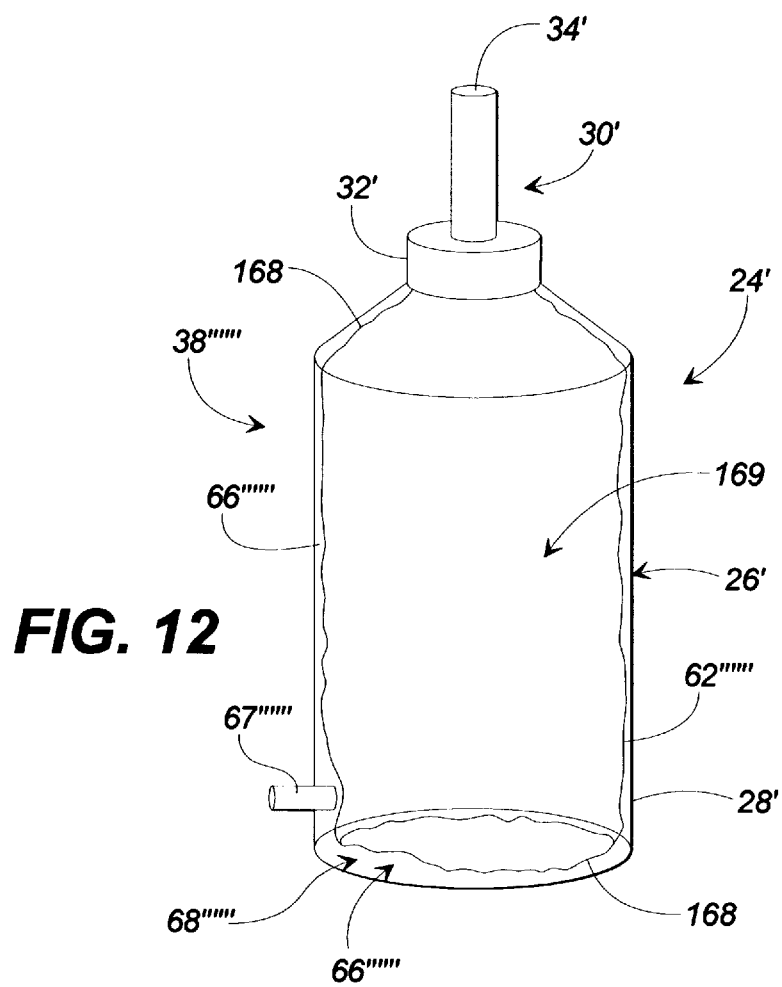
FIG. 12 is an isolated, schematic, perspective view of a combined receptacle and container assembly in accordance with a seventh preferred embodiment of the present invention.

FIG. 12 is an isolated, schematic, perspective view of a combined receptacle 38''''' and container assembly 24' used in place of the receptacle 38 and container assembly 24 of FIG. 1 in accordance with a seventh preferred embodiment of the present invention. As depicted in FIG. 12, the container assembly 24' is similar to the container assembly 24 (FIGS. 1 and 2) that is disclosed in U.S. Pat. No. 2,869,545, which patent has been incorporated by reference. However, the present invention is not limited to the container assembly disclosed in the aforementioned patent, as various containers and container assemblies are within the scope of the present invention.

In accordance with the seventh preferred embodiment of the present invention, the inflation device 58''''' is in the form of an inner wall 62'''''. The inner wall 62''''' defines a container that is acceptably in the form of a collapsible bag 168 or sac that at least partially bounds a chamber 169 for containing the fluid. When the combined receptacle 38''''' and container assembly 24' is fully assembled as depicted in FIG. 12, the chamber 169 communicates solely through the nozzle 30'.

Figure 13:
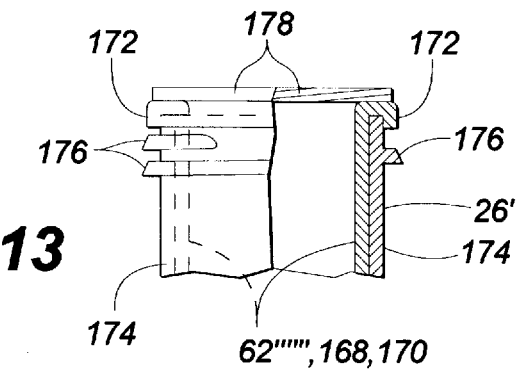
FIG. 13 is an isolated, cut-away, and partially sectioned view of a portion of the combined receptacle and container assembly of FIG. 12.

FIG. 13 is an isolated, cut-away, and partially sectioned view of a portion of the combined receptacle 38''''' and container assembly 24'. The container 26' defines a generally annular neck 174 that defines an opening to the container 26. The bag 168 tapers to a generally annular neck 170 that defines a passage therethrough to the chamber 169 within the bag 168. The neck 170 terminates in the form of a generally annular lip 172. The neck 170 of the bag 168 extends through the neck 174 of the container 26' and the lip 172 is wrapped downward about the upper rim of the neck 174 of the container 26' to generally occlude the opening to the container 26' that is defined by the neck 174 of the container 26. The neck 174 of the container 26' defines external threads 176 for engaging internal threads defined in the cap 32', and the cap 32' typically covers and conceals the necks 170,174. Referring to FIGS. 12 and 13, an inflation chamber 66''''' is defined between the wall 28' of the container 26' and the bag 168 such that substantially the only communication path to the inflation chamber 66''''' is through a fitting 67''''' extending through the wall 28'. In accordance with the seventh embodiment, a valve such as, but not limited to, a flexible disk 178 (FIG. 13) with a slit therethrough is situated above the lip 172, and when the cap 32' is threaded onto the neck 170 of the container 26' the lip 172 and disk 178 are compressed by the cap 32' and thereby secured in place.

Figure 14:
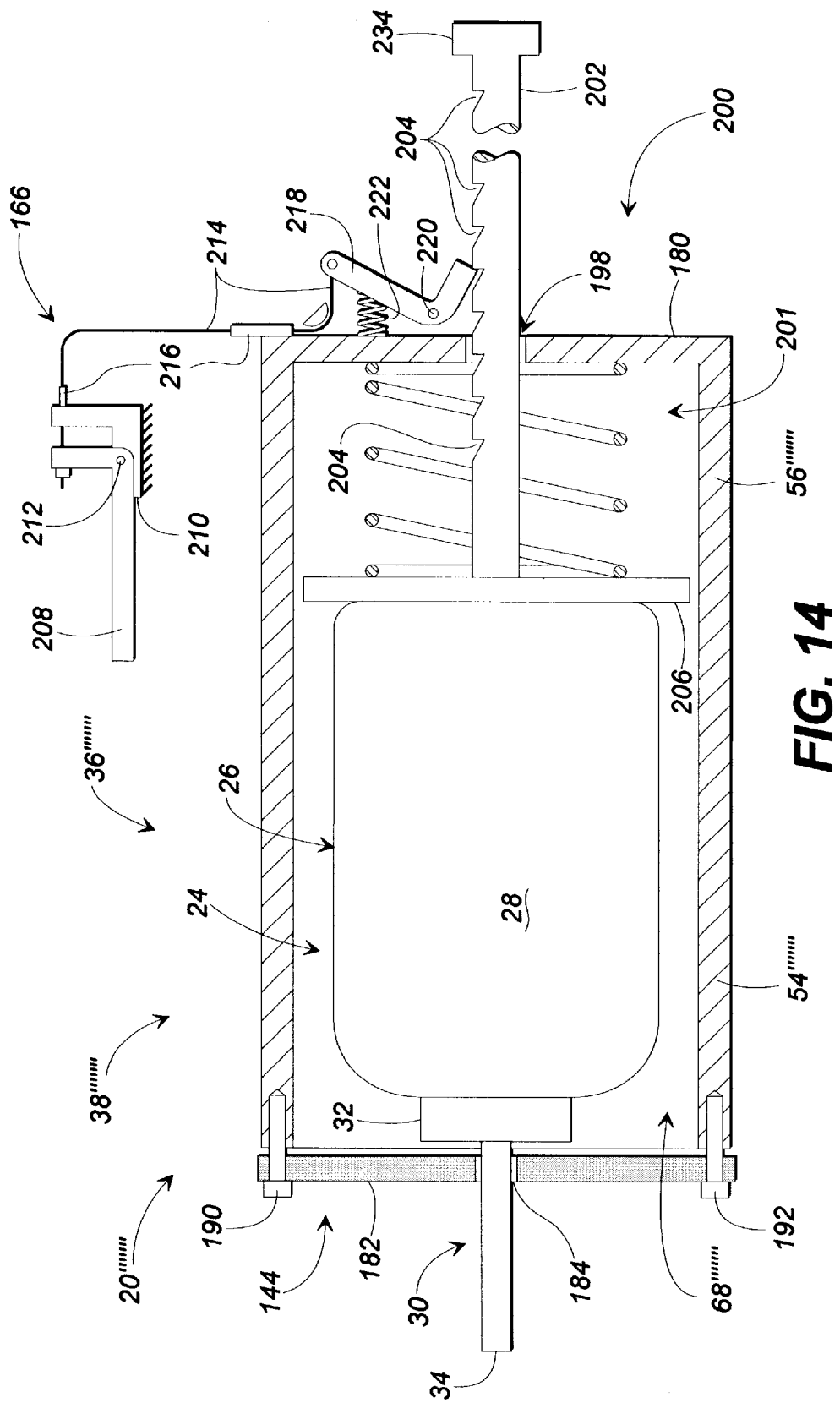
FIG. 14 is a schematic diagram of an applicator assembly in accordance with an eighth embodiment of the present invention.

FIG. 14 is a schematic diagram of an applicator assembly 20''''''' in accordance with an eighth embodiment of the present invention. The applicator assembly 20''''''' includes a compressing device 36''''''' that includes a receptacle 38''''''' that receives and compresses the container 26 to force the fluid out of the container 26 through the nozzle opening 34, as discussed in greater detail below. The applicator assembly 20''''''' further includes a linkage assembly 166, or the like, associated with the compressing device 36''''''' for controlling or activating the compression device 36''''''' as discussed in greater detail below.

Figure 15:
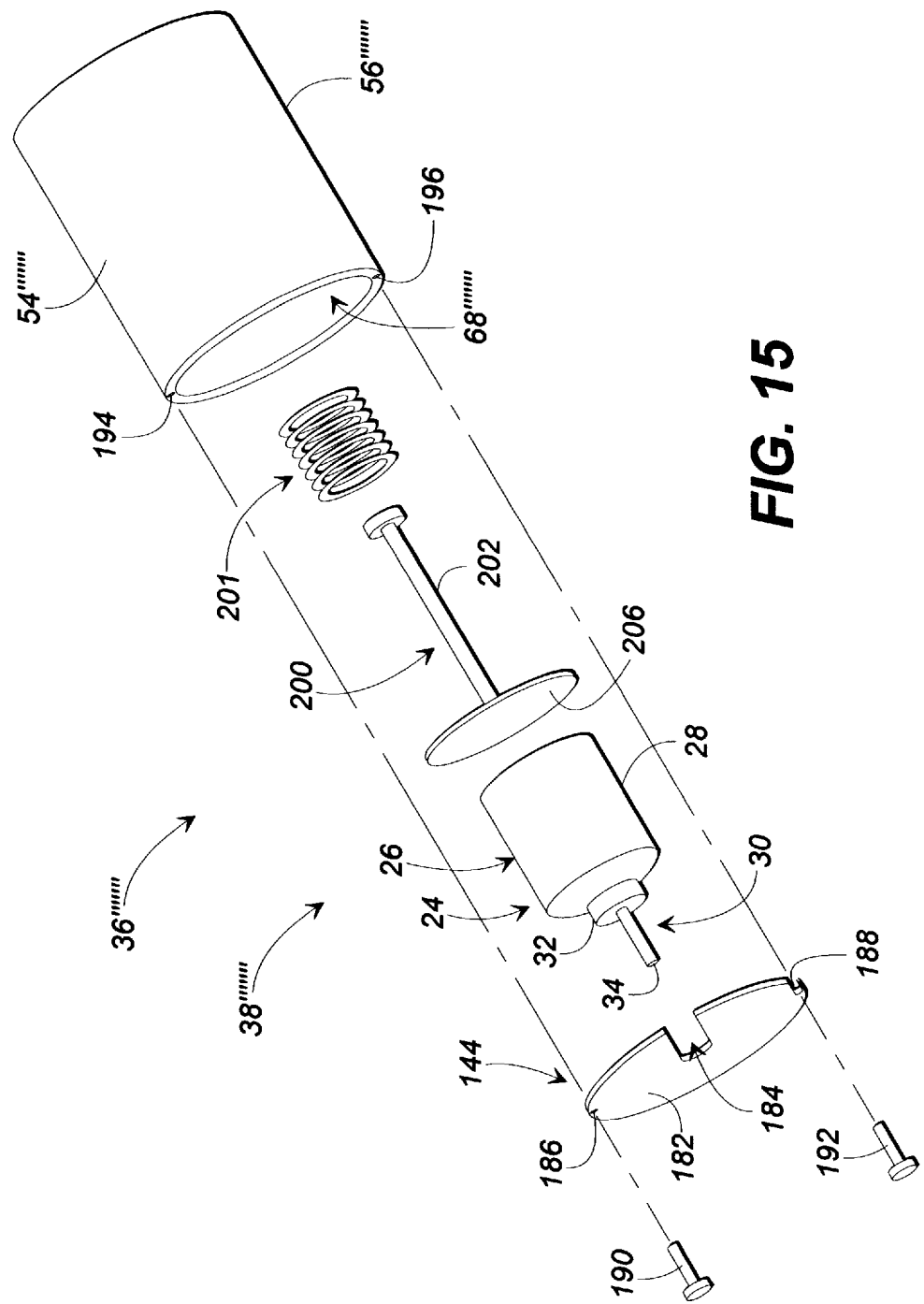
FIG. 15 is an isolated, schematic, exploded view of a container and a compressing device of the applicator assembly of FIG. 14.

FIG. 15 is an isolated, schematic, exploded view of the compressing device 36' ''''' in accordance with the eighth embodiment of the present invention. Referring to both FIGS. 14 and 15, the receptacle 38''''''' includes an outer wall 54''''''' that is in the form of an outer tube 56''''''' that generally defines an internal bore that serves as the receptacle cavity 68''''''' which receives the container assembly 24. For example and not limitation, an acceptable container assembly 24 is disclosed in U.S. Pat. No. 2,869,545, which has been incorporated by reference. An end wall 180 or cap is preferably connected to or contiguous with the outer tube 56''''''' to occlude one end of the tube 56''''''', and a removable plate assembly 144 like that depicted in FIG. 11 removably occludes the other end of the tube 56'''''''. The plate assembly 144 includes a plate 182 that defines a middle aperture 184 therethrough for receiving the nozzle 30, and two side apertures 186,188 therethrough for receiving bolts 190,192, or the like, that pass through the side apertures 186,188 and removably thread into apertures 194,196 defined in the tube 56'''''''. By virtue of the fact that aperture 188 is in the form of a slot that extends to the side of the plate 182, the bolts 190,192 can be loosened slightly and then the plate can be pivoted about bolt 190 to selectively occlude and provide access to the receptacle cavity 68''''''' defined within the tube 56'''''''. Alternately a latching mechanism is provided that cooperates with the plate 182 to selectively hold the plate 182 in place.

The end wall 180 defines a central aperture 198 therethrough. A linkage or plunger assembly 200 that transfers movement of a coil spring 201 to compress the container 26. The plunger assembly 200 includes a rod 202 that extends through the aperture 198 and defines a plurality of notches 204 along its length. Only a select few of the notches 204 are specifically identified in FIG. 14 in an effort to clarify the view. The spring 201 encircles the rod 202 and is interposed between the rear wall 180 and a plate 206 that is connected to the end of the rod 202. The plate 206 is for contacting and compressing the container 26 in response to movement of the spring 201. The spring 201 is biased toward an expanded configuration which tends to force the plate 206 toward the removable plate assembly 144.

Referring to FIG. 14, expansion of the spring 201 is controlled by cooperation between the linkage assembly 166 and the notches 204. That is, the linkage assembly 166 functions to activate the compressing device 36'''''''. In accordance with the eighth preferred embodiment, the linkage assembly 166 preferably includes a remotely positioned L-shaped lever 208 that pivots about a pivot pin 212 relative to a reference member 210. A cable 214 is connected to the lever 208 distant from the pivot pin 212. The cable 214 passes through various sheaths 216 and is connected to another L-shaped lever 218 that is pivotally connected to the rear wall 180 by a pivot pin 220. One end of the lever 218 is connected to the cable 214 while the opposite end of the lever 218 is biased toward engagement with notches 204 by a spring 222 cooperatively mounted between the lever 218 and the rear wall 180. While the nozzle 30 is inserted into a cavity and the spring 201 is compressed, the lever 208 is preferably remotely actuated (i.e., pivoted counterclockwise from the position depicted in FIG. 14). That cause the lever 218 to actuate (i.e., pivot counterclockwise from the position depicted in FIG. 14) and disengage from the notches 204. As a result, the spring expands such that the container 26 is compressed and fluid is forced out of the nozzle 30.

Figure 16:
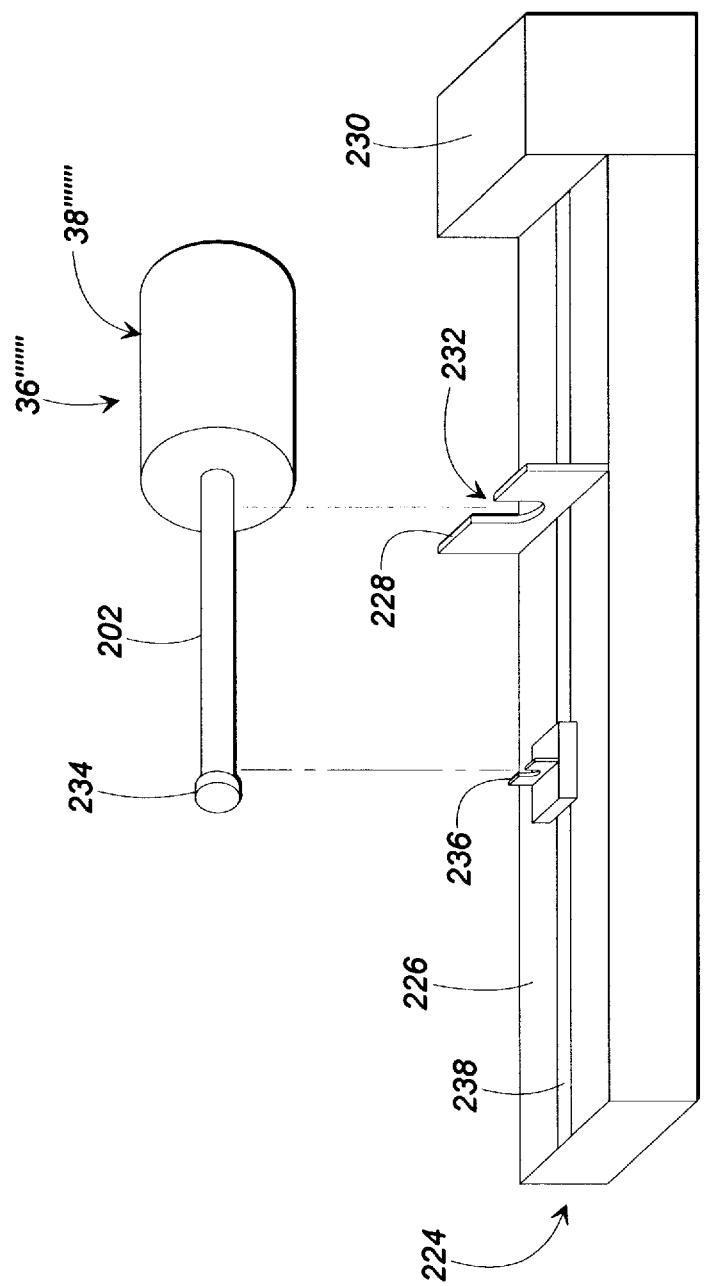
FIG. 16 is a perspective view of the compressing device of FIG. 15 disposed above a cocking assembly, in accordance with an eighth embodiment of the present invention.

FIG. 16 is a perspective view of the compressing device 36'"'" disposed above a cocking assembly 224 that functions to compress the spring 201 (FIGS. 14 and 15). When the spring 201 is compressed, the lever 218 (FIG. 14) engages a notch 204 (FIG. 14) to maintain the spring 201 in the compressed configuration. The cocking assembly includes a top surface 226, and a somewhat U-shaped stationary member 228 extends upward from the top surface 226. The receptacle 38'"'" portion of the compressing device 36'"'" is placed upon the top surface 226 and interposed between the stationary member 228 and an upward extending rear portion 230. The rod 202 fits through an aperture 232 defined in the stationary member 228 such that the rod 202 is capable of being drawn from within the receptacle 38'"'" while the receptacle 38'"'" is maintained stationary. A flange 234 at the end of the rod 202 fits over a somewhat U-shaped member 236 that moves in a track 238 toward and away from the stationary member 228. The flange 234 is generally restrained to the member 236 such that when the member 236 is moved away from the stationary member 228, the spring 201 is compressed and the linkage assembly 166 (FIG. 14) cooperates with the notches 204 in the rod 202 to maintain the spring 201 in the compressed configuration. Movement of the member 236 is acceptably achieved, for example and not limitation, by a pneumatic cylinder or a linearly actuating electric motor disposed within the cocking assembly.

While the embodiments of the present invention which have been disclosed herein are the preferred forms, other embodiments of the method and apparatus of the present invention will suggest themselves to persons skilled in the art in view of this disclosure. Therefore, it will be understood that variations and modifications can be effected within the spirit and scope of the invention and that the scope of the present invention should only be limited by the claims below. It is also understood that any relationships shown on the drawings are given as the preferred relative relationships, but the scope of the invention is not to be limited thereby.

I claim:

1. An automated method for personally ejecting fluid from a container, through a nozzle communicating with said container, and then into a posterior cavity of a person's body, where said person has limited dexterity and strength to otherwise perform such function, the method comprising the steps of:

positioning a compression mechanism remote from said posterior cavity;

disposing said container within said mechanism;

inserting said nozzle into said posterior cavity;

actuating said mechanism to set said mechanism into motion; and harnessing the motion of said mechanism to automatically force said fluid from said container through said nozzle into said posterior cavity.

2. The method of claim 1, wherein the method further comprises a step of mounting the container proximate to an inflation device, and wherein the harnessing includes a step of inflating the inflation device so that the inflation device expands and compresses the container to force the fluid from the container and through the nozzle into the cavity.

3. The method of claim 1, wherein the method further comprises the steps of compressing a spring and retaining the spring in its compressed state, and mounting the container proximate to the spring, wherein the harnessing step includes a step of releasing the spring from the compressed state, whereby the spring expands, and wherein the harnessing step includes a step of controlling the expansion of the spring so that the spring expands and compresses the container to force the fluid from the container and through the nozzle into the cavity.

* * * * *